United States Patent [19]
Barath

[11] Patent Number: 5,797,935
[45] Date of Patent: Aug. 25, 1998

[54] BALLOON ACTIVATED FORCED CONCENTRATORS FOR INCISING STENOTIC SEGMENTS

[75] Inventor: Peter Barath, Hinsdale, Ill.

[73] Assignee: Interventional Technologies Inc., San Diego, Calif.

[21] Appl. No.: 721,597

[22] Filed: Sep. 26, 1996

[51] Int. Cl.⁶ ..................................................... A61B 17/22
[52] U.S. Cl. ........................................... 606/159; 606/170
[58] Field of Search ................................. 606/159, 170, 606/191, 194, 167, 198; 604/96

[56] References Cited

U.S. PATENT DOCUMENTS

| | | | |
|---|---|---|---|
| 5,336,234 | 8/1994 | Vigil et al. | 606/159 |
| 5,616,149 | 4/1997 | Barath | 606/159 |

Primary Examiner—Michael Buiz
Assistant Examiner—Kevin Truong
Attorney, Agent, or Firm—Michael E. Klicpera

[57] ABSTRACT

A balloon activated force concentrator for use in cooperation with an inflatable angioplasty balloon includes at least one elongated flexible panel, an elongated cutting blade mounted on the outside surface of the elongated flexible panel, and an elastic circular band attached to each end of the elongated flexible panel for securing the elongated flexible panel to an angioplasty balloon. Use of this balloon activated force concentrator requires mounting the device on an inflatable angioplasty balloon by inserting the distal end of the angioplasty balloon through one of the circular bands. The balloon activated force concentrator is then advanced over the balloon until the second circular band reaches the distal end of the balloon. At that point, the elasticity of the circular bands straddle the balloon to retain the activated force concentrator securely against the outer surface of the angioplasty balloon.

19 Claims, 2 Drawing Sheets

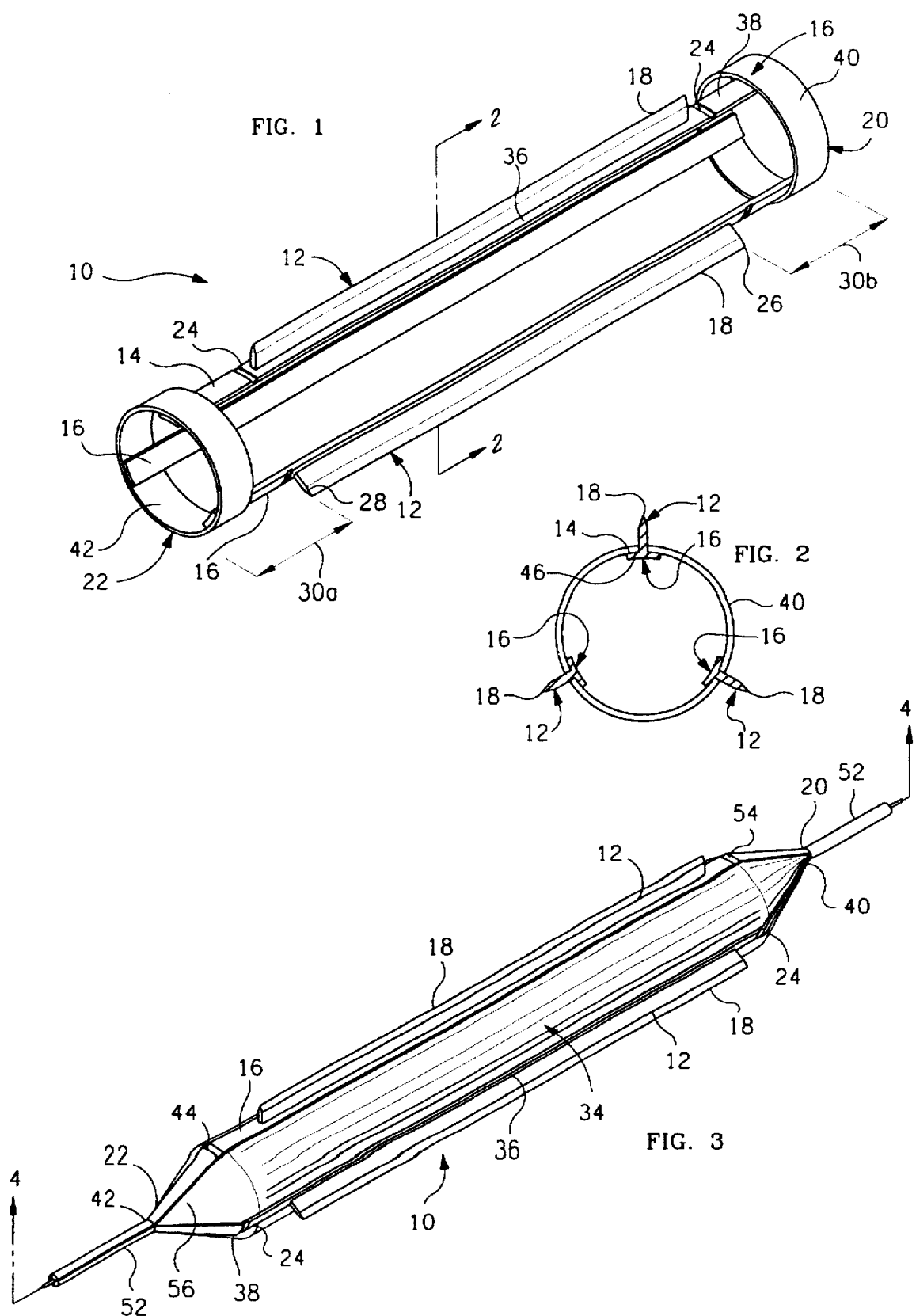

BALLOON ACTIVATED FORCED CONCENTRATORS FOR INCISING STENOTIC SEGMENTS

FIELD OF INVENTION

The present invention relates generally to surgical instruments. More particularly, the present invention pertains to invasive surgical devices which are useful for the incision and dilation of stenoses in a vessel. The present invention is particularly, though not exclusively, useful in cooperation with an angioplasty balloon for incising a stenosis to assist and facilitate subsequent dilation of the stenosis.

BACKGROUND OF INVENTION

The blockage of human arteries can lead to a variety of serious medical complications. This is so because arterial blockages reduce blood flow through the affected artery and may result in damage to the tissue that is relying on the blood supply. For example, if the blockage is in an artery which supplies blood to the heart itself, a heart attack may result.

Such arterial blockages, which are also called stenoses, are typically caused by the build-up of atherosclerotic plaque on the inside wall of an artery. In fact, several such stenoses may occur contiguously within a single artery. This can result in a partial, or even complete, blockage of the artery. As a result of the danger associated with such a blockage, several methods and procedures have been developed to treat stenoses. One such method is an angioplasty procedure which uses an inflatable balloon to dilate the blocked artery. A typical inflatable angioplasty device, for example, is disclosed in U.S. Pat. No. 4,896,669 which issued to Bhate et al. for an invention entitled "DILATION CATHETER. The Bhate et al angioplasty device includes an inflatable angioplasty balloon which is insertable into a peripheral artery of a patient for positioning across a stenosis. Once positioned, the angioplasty balloon is then inflated to flatten the stenosis against the inside wall of the artery thereby improving the blood flow through the artery.

Angioplasty balloons have enjoyed widespread acceptance in the treatment of stenoses. Recent studies, however, have indicated that the efficacy of the dilation of a stenosis is enhanced by first, or simultaneously, incising the material that is creating the stenosis. Consequently, recent developments have been made to equip angioplasty balloons with cutting edges, or atherotomes, which are intended to incise a stenosis during the dilation procedure. For example, the device disclosed in U.S. Pat. No. 5,196,024 to Barath entitled "BALLOON CATHETER WITH CUTTING EDGE," which is assigned to the assignee of the present invention, is an inflatable angioplasty balloon having a number of atherotomes mounted longitudinally on the surface of the balloon. Upon inflation of the Barath balloon, the atherotomes induce a series of longitudinal cuts into the surface of the stenotic material as the balloon expands to dilate the stenosis. As a result of such cuts, the stenosis is more easily flattened, and the likelihood of damaging the artery during dilation is reduced.

Although there are numerous benefits associated with the use of angioplasty balloons which are equipped with atherotomes, it is sometimes preferable to use a balloon that is not so equipped. Moreover, it is often necessary to use various sized angioplasty balloons to dilate correspondingly different sized vessels. Thus, in order to be fully prepared for an angioplasty procedure, a substantial inventory of angioplasty balloons must be on hand.

One way to minimize the inventory necessary for a single angioplasty procedure would be to decrease the variety of angioplasty balloons which are required to be on hand during the procedure. This inventory minimization may be achieved by allowing a user to customize a single angioplasty balloon for a variety of applications. More specifically, by providing removable atherotomes which may be selectively attached to an angioplasty balloon, it would be possible to configure an appropriately sized balloon with the proper atherotome. As a result of this ability to customize a single angioplasty balloon for a variety of procedures, the substantial inventory required for an angioplasty procedure would be significantly reduced.

In light of the above, it is an object of the present invention to provide a device for incising a stenosis in a vessel of a patient which is useable in cooperation with an inflatable angioplasty balloon. It is a further object of the present invention to provide a cutting blade which is capable of being removably mounted on an inflatable angioplasty balloon. It is another object of the present invention to provide a device for incising a stenosis in a vessel which is relatively simple to manufacture, is easy to use, and is comparatively cost effective.

SUMMARY OF INVENTION

In accordance with the present invention, a device which is mountable on an angioplasty balloon for incising a stenosis is provided. More specifically, the device includes a plurality of elongated cutting blades which are longitudinally mountable on the outer surface of an angioplasty balloon. Each of these cutting blades has a cutting edge which extends away from the outer surface of the balloon so that the cutting edge moves radially outward to incise the stenosis when the angioplasty balloon is inflated.

In order to insure the cutting blades are longitudinally aligned on the surface of the angioplasty balloon, each cutting blade is securely attached to a respective elongated flexible panel so that the cutting edge extends outwardly from the panel. Each elongated flexible panel extends the length of the angioplasty balloon and is attached at its respective ends to a pair of circular bands. These circular bands are made of an elastic material which allows the device to be removably positioned over the angioplasty balloon.

The use of the device of the present invention includes mounting the device on an angioplasty balloon. This mounting of the device on the balloon is accomplished by inserting the deflated angioplasty balloon through one of the circular bands and sliding the device over the balloon until the balloon reaches the second circular band. At that point, the elastic circular bands straddle the balloon to retain the device in place against the outer surface of the balloon.

Once the device is mounted on the angioplasty balloon, the combination of the device and balloon are inserted into the vessel of a patient and positioned across the stenosis. The angioplasty balloon is then slowly inflated, causing the cutting blades of the device to move outwardly in a radial direction to incise the stenosis and dilate the vessel. The balloon is then deflated and the combination of the angioplasty balloon and the balloon activated force concentrator are removed from the vessel and the patient.

BRIEF DESCRIPTION OF THE DRAWINGS

The novel features of this invention, as well as the invention itself, both as to its structure and its operation will be best understood from the accompanying description, in which similar reference characters refer to similar parts, and in which:

FIG. 1 is a perspective view of the present invention;

FIG. 2 is a cross-sectional view of the present invention as seen along line 2—2 in FIG. 1;

FIG. 3 is a perspective view of the present invention in combination with an inflatable angioplasty balloon;

DESCRIPTION OF PREFERRED EMBODIMENTS

Figure 4:
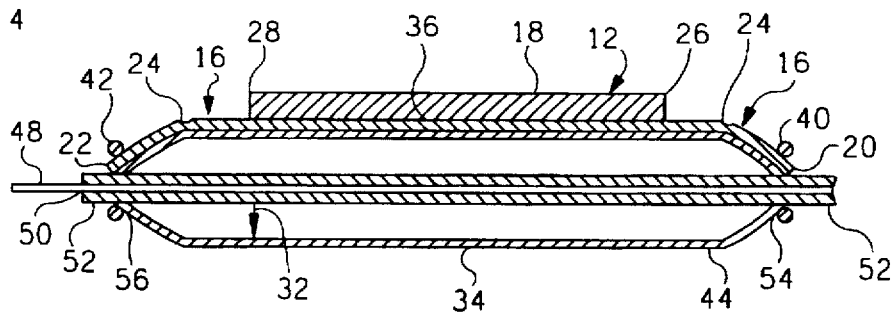
FIG. 4 is a cross-sectional view of the present invention in combination with an inflated angioplasty balloon, as seen along line 4—4 in FIG. 3.

Referring initially to FIG. 1, the balloon activated force concentrator of the present invention is shown and is generally designated 10. A rigid cutting blade 12 is firmly attached to, and extends perpendicularly from, the outside surface 14 of each elongated flexible panel 16. This cutting blade 12 is formed from a rigid material which tapers to a cutting edge 18 at its most radial point. Attachment of the cutting blade 12 to the elongated flexible panel 16 may be accomplished using a variety of methods. For example, the cutting blade 12 may be pre-formed and then mounted onto the elongated flexible panel 16 using an adhesive. Alternatively, the elongated flexible panel 16 may be formed with the cutting blade 12 in place. In either case, the cutting blade 12 is permanently mounted on the outer surface 14 of the elongated flexible panel 16.

It is to be appreciated from FIG. 1 that the elongated flexible panel 16 is the main structural support member for the balloon activated force concentrator 10. Importantly, the elongated flexible panel 16 is made of a material which allows the ends 20, 22 of the panel 16 to resiliently bend. More specifically, the elongated flexible panel 16 is made of a spring-like material which, although capable of bending, has a strong tendency to return to its original shape. In order to assist this bending and insure that it occurs in a proper location, detents 24 are formed on the outside surface 14 of the elongated flexible panel 16. More specifically, a detent 24 is formed between the proximal end 26 of the cutting blade 12 and the proximal end 20 of the elongated flexible panel 16. Likewise, a detent 24 is formed between the distal end 28 of the cutting blade 12 and the distal end 22 of the elongated flexible panel 16.

Note that there is a setback distance 30a and 30b respectively between each end 26, 28 of the cutting blade 12 and each respective end 20, 22 of the elongated flexible panel 16. This setback distance 30 is preferably at least twice the radius 32 of the inflatable angioplasty balloon 34 when inflated (shown in FIG. 4)A In other words, the setback distance 30b from the proximal end 20 of the elongated flexible panel 16 to the proximal end 26 of the cutting blade 12 should be about twice the radius 32 of the inflated angioplasty balloon 34. Similarly, the setback distance 30a from the distal end 22 of the elongated flexible panel 16 to the distal end 28 of the cutting blade 12 should be about twice the radius 32 of the inflated angioplasty balloon 34. The importance of the setback distances 30a and 30b is due to the rigidity of the cutting blade 12 which prevents the portions 36 of the elongated flexible panel 16 immediately adjacent to the rigid cutting blade 12 from bending. Thus, only flexible portions 38 of the elongated flexible panel 16 will bend to conform with the inflatable angioplasty balloon 34 (not shown in FIG. 1).

FIG. 1 also provides a clear view of the proximal circular band 40 attached to the proximal end 20 of the elongated flexible panel 16, and the distal circular band 42 attached to the distal end 22 of the elongated flexible panel 16. Both circular bands 40, 42 are made of an expandable material which allows them to be stretched, yet insures they return to their original size. As can be appreciated with reference to FIG. 5, these circular bands 40, 42 are sized to be slidable over the outside surface 44 of an un-inflated angioplasty balloon 34 for proper positioning of the balloon activated force concentrator 10. These circular bands 40, 42 may be made of any bio-compatible material which will provide a gripping force around the angioplasty balloon 34. Such materials may include, for example, elastic bands, metal spring clips, or circular springs.

Referring now to FIG. 2, a cross section of the balloon activated force concentrator 10 shows the cutting blade 12, the elongated flexible panels 16, and the proximal circular band 40. More specifically, cutting blade 12 extends perpendicularly from the outer surface 14 of the elongated flexible panel 16 so that when the device 10 is mounted on an angioplasty balloon 34 (not shown in FIG. 2), the cutting edge 18 will move radially outward when the balloon 34 is inflated. Also shown in this FIG. 2, the proximal circular band 40 is shown encircling several of the elongated flexible panels 16. Note that the circular band 40 could be attached to the inner surface 46 of the elongated flexible panel 16 instead of the outer surface 14.

Referring now to FIG. 3, the balloon activated force concentrator 10 of the present invention is shown mounted on an inflated angioplasty balloon 34. More specifically, the elongated flexible panels 16, with an associated cutting blade 12, are shown mounted on the outside surface 44 of an inflated angioplasty balloon 34. Further, a proximal circular band 40 and a distal circular band 42 are attached to the respective ends 20, 22 of the elongated flexible panel 16. This is done to retain the elongated flexible panel 16, and associated cutting blades 12, in a longitudinal alignment with the angioplasty balloon 34. As discussed above in connection with FIG. 2, such placement against the angioplasty balloon 34 provides that upon inflation of the angioplasty balloon 34, the elongated flexible panel 16, and the associated cutting blade 12, will move outwardly in a radial direction. Also, the importance of the setback distance 30, mentioned above in connection with FIG. 1, can be readily appreciated from this figure. More specifically, the setback distance 30 insures that the elongated flexible panels 16 will be capable of bending to conform with the outer surface 44 of the angioplasty balloon 34 when inflated. The setback distance 30, however, may be determined for any particular angioplasty balloon 34 and need not be limited to twice the radius 32 of the inflated angioplasty balloon 34.

FIG. 4 is a cross-sectional view of the balloon activated force concentrator 10 shown as used in cooperation with an inflated angioplasty balloon 34. More specifically, FIG. 4 shows the elongated flexible panel 16 bending to conform with the outside surface 44 of the angioplasty balloon 34. Such bending of the proximal end 20 and the distal end 22 of the elongated flexible panel 16 is possible because of the maintenance of the setback distance 30. To this end, the detents 24 are located on the elongated flexible panel 16 to insure that the elongated flexible panel 16 bends in a predictable location.

Figure 5:
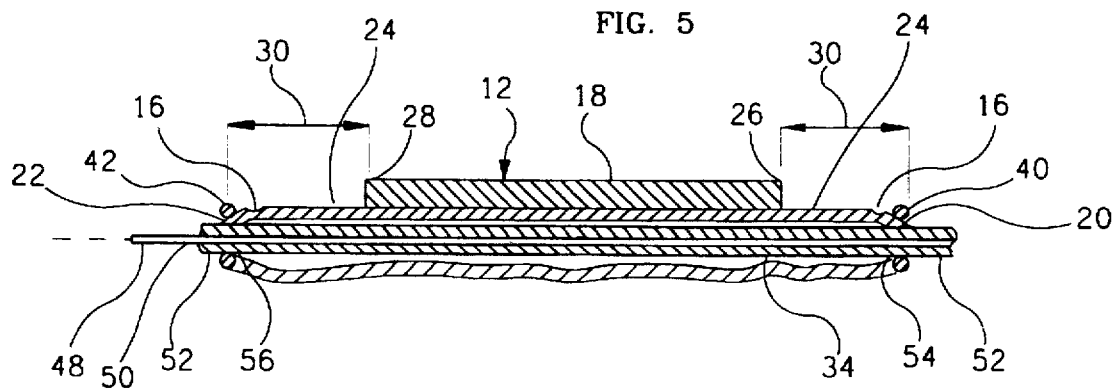
FIG. 5 is a cross-sectional view of the present invention viewed as in FIG. 4 with the present invention in combination with a deflated angioplasty balloon.

Referring now to FIG. 5, the balloon activated force concentrator 10 is shown mounted on a deflated angioplasty balloon 34. From this FIG. 5, and with cross-reference to FIG. 4, the flexible nature of the elongated flexible panel 16 may be fully appreciated. Additionally, the method of mounting the balloon activated force concentrator 10 may be easily understood. More specifically, mounting the balloon activated force concentrator 10 begins with the insertion of the distal end 56 of the angioplasty balloon 34 through the proximal circular band 40. The balloon activated force concentrator 10 is then advanced proximally over the angioplasty balloon 34 until the distal circular band 42 reaches the distal end 56 of the angioplasty balloon 34. At that point, the elastic nature of the proximal circular band 40 and distal circular band 42 causes them to straddle the catheter 52. Thus, the balloon activated force concentrator 10 is retained in position by a gripping force generated by the elastic nature of the circular bands 40, 42. In an alternative embodiment, a metal clip, circular spring, or any other retention device, may be used instead of the circular bands 40, 42 to retain the elongated flexible panel 16 against the outer surface 44 of the angioplasty balloon 34.

Figure 6:
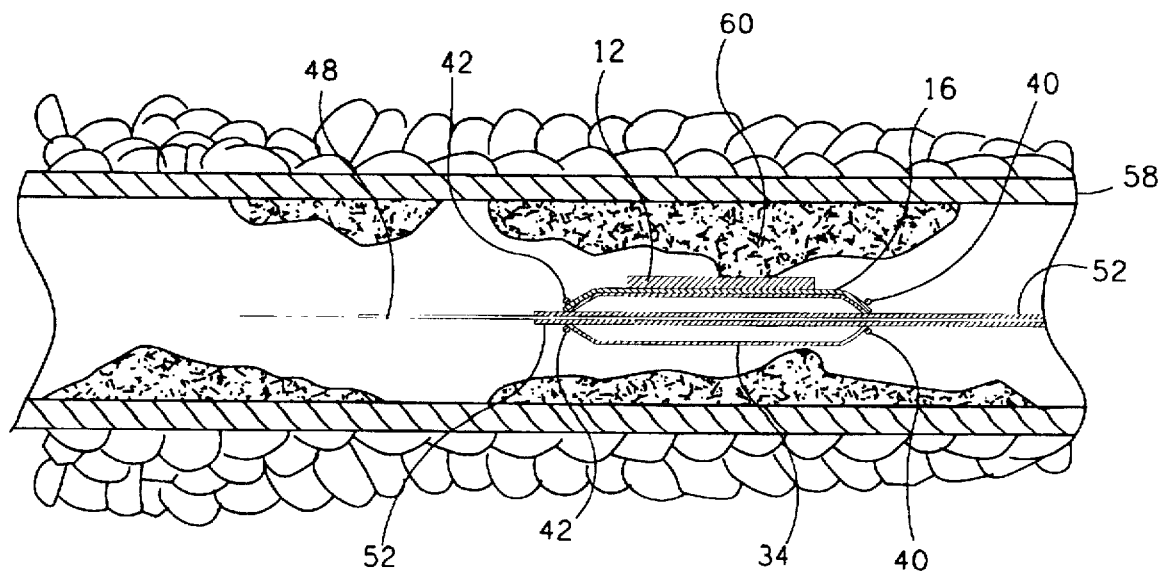
FIG. 6 is a cross-sectional view of the present invention in its intended environment as used in cooperation with an inflatable angioplasty balloon.

Referring now to FIG. 6, the balloon activated force concentrator 10 is shown being used in its intended environment. More specifically, the balloon activated force concentrator 10 is shown mounted on an angioplasty balloon 34, with the combination having been inserted into a vessel 58 and advanced along the guide wire 48 for positioning across a stenosis 60. Upon proper positioning, the angioplasty balloon 34 is inflated causing the elongated flexible panel 16, and the corresponding cutting blade 12, to move outwardly in a radial direction. As the cutting blade 12 moves radially outward, it creates longitudinal incisions in the stenosis 60 allowing the angioplasty balloon 34 to dilate the vessel 58. Following dilation of the vessel 58, the angioplasty balloon 34 is deflated, causing the balloon activated force concentrator 10 to return to its original shape. The combination of the angioplasty balloon 34, and balloon activated force concentrator 10, is then removed from the vessel 58 and patients.

While the particular balloon activated force concentrator 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for incising stenotic segments, mountable over an inflatable angioplasty balloon, which comprises:
    at least one elongated flexible panel, said panel having an outer surface, an inner surface, a proximal end and a distal end;
    a cutting blade having an edge, said cutting blade mounted on said outer surface of said elongated flexible panel with said edge of said cutting blade projecting away from said outer surface of said elongated flexible panel;
    a first circular band attached to said proximal end of each said elongated flexible panel; and
    a second circular band attached to said distal end of each said elongated flexible panel, said first circular band and said second circular band being positionable to retain said inner surface of each said elongated flexible panel against said angioplasty balloon.

2. A device as recited in claim 1, wherein said cutting blade further comprises:
    a proximal end, said proximal end of said cutting blade being separated a first predetermined distance from said proximal end of said elongated flexible panel; and
    a distal end, said distal end of said cutting blade being separated a second predetermined distance from said distal end of said elongated flexible panel.

3. A device as recited in claim 2 wherein said first predetermined distance and said second predetermined distance are substantially equal.

4. A device as recited in claim 2, wherein said angioplasty balloon has a radius when inflated and said first predetermined distance is approximately equal to twice said inflated radius of said inflatable angioplasty balloon.

5. A device as recited in claim 1, wherein said cutting blade is made of stainless steel.

6. A device as recited in claim 1, wherein said cutting blade is made of cobalt nickel steel.

7. A device as recited in claim 1, wherein said cutting blade is made of a ceramic material.

8. A device as recited in claim 1, wherein said cutting blade is made of a glass material.

9. A device as recited in claim 1, wherein said elongated flexible panel is made of dacron fiber and urethane.

10. A device as recited in claim 1, wherein said elongated flexible panel is made of a spring-like material.

11. A device as recited in claim 1 wherein said first circular band is formed from an elastic material.

12. A device as recited in claim 1 wherein said first circular band and said second circular band are formed from an elastic material.

13. A device for incising stenotic segments, comprising:
    a balloon moveable between a collapsed configuration and an inflated configuration;
    a plurality of elongated flexible panels, each said panel having an outer surface, a proximal end and a distal end;
    a plurality of cutting means, each said cutting means being firmly attached to said outer surface of a respective said elongated flexible panel; and
    a retaining means for collectively securing said plurality of elongated flexible panels to said balloon with said cutting means projecting radically away from said balloon and for movement therewith, to incise said stenotic segments when said balloon is in said inflated configuration wherein said retaining means comprises a first circular band attached to said proximal end of each said elongated flexible panel and a second circular band attached to said distal end of each said elongated flexible panel.

14. A device as recited in claim 13, wherein said cutting means further comprises at least one cutting blade, said cutting blade having a cutting edge and a base, said base being firmly attached to said outer surface of said elongated flexible panel, and in substantial alignment therewith, to hold said cutting edge away from said elongated flexible panel.

15. A device as recited in claim 13, wherein said first circular band is made of an elastic material.

16. A device as recited in claim 15, wherein said second circular band is made of an elastic material.

17. A device as recited in claim 13, wherein said first and second circular bands are made of a rigid material.

18. A device as recited in claim 13, wherein said retaining means further comprises a pair of rigid circular clamps, one said clamp attached to said proximal end of said elongated flexible panel, and one said clamp attached to said distal end of said elongated flexible panel.

19. A method for operating a cutting device with an angioplasty balloon to incise and dilate a stenotic segment in a vessel, wherein the cutting device includes a plurality of elongated flexible panels with each panel having a proximal end and a distal end and a cutting blade mounted thereon, and wherein the proximal and distal ends of each flexible panel are respectively attached to a proximal band and a distal band, the method comprising the steps of:

positioning said proximal band and said distal band of said cutting device to straddle said balloon with said panels retained therebetween against said balloon and with said cutting blades projecting away from said balloon; and inflating said balloon to move said flexible panels and said cutting blades therewith for incising and dilating the stenotic segment as said balloon is inflated.

* * * * *